US00PP27478P3

(12) United States Plant Patent
Yamada

(10) Patent No.: US PP27,478 P3
(45) Date of Patent: Dec. 20, 2016

(54) ***CATHARANTHUS* PLANT NAMED 'SUNCATHA 224'**

(50) Latin Name: *Catharanthus roseus*
Varietal Denomination: Suncatha 224

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 44 days.

(21) Appl. No.: 14/545,155

(22) Filed: Mar. 31, 2015

(65) Prior Publication Data

US 2016/0295768 P1 Oct. 6, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Catharanthus* plant named 'Suncatha 224', characterized by its upright to outwardly spreading and mounding plant habit; vigorous growth habit; freely basal branching habit; freely flowering habit; long flowering period; relatively small red purple-colored flowers; and good garden performance.

1 Drawing Sheet

Botanical designation: *Catharanthus roseus.*
Cultivar denomination: 'SUNCATHA 224'.

BACKGROUND OF THE INVENTION

The present invention relates to a new and distinct *Catharanthus* plant, botanically known as *Catharanthus roseus* and hereinafter referred to by the cultivar name 'Suncatha 224'.

The new *Catharanthus* plant is a product of a planned breeding program conducted by the Inventor in Yame, Fukuoka, Japan. The objective of the breeding program is to develop new freely branching and vigorous *Catharanthus* plants with numerous attractive flowers.

The new *Catharanthus* plant originated from a cross-pollination conducted by the Inventor in Yame, Fukuoka, Japan in September, 2010 of a proprietary selection of *Catharanthus roseus* identified as code designation FS-S, not patented, as the female, or seed, parent with a proprietary selection of *Catharanthus roseus* identified as code designation NCPS, not patented, as the male, or pollen, parent. The new *Catharanthus* plant was discovered and selected by the Inventor as a single flowering plant from within the progeny of the stated cross-pollination in a controlled greenhouse environment in Yame, Fukuoka, Japan in February, 2011.

Asexual reproduction of the new *Catharanthus* plant by vegetative tip cuttings in a controlled greenhouse environment in Yame, Fukuoka, Japan since February, 2011, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncatha 224'. These characteristics in combination distinguish 'Suncatha 224' as a new and distinct *Catharanthus* plant:

1. Upright to outwardly spreading and mounding plant habit.
2. Vigorous growth habit.
3. Freely basal branching habit.
4. Freely flowering habit.
5. Long flowering period.
6. Relatively small red purple-colored flowers.
7. Good garden performance.

Plants of the new *Catharanthus* can be compared to plants of the female parent selection. Plants of the new *Catharanthus* differ primarily from plants of the female parent selection in flower petal color as plants of the female parent selection have red-colored flower petals.

Plants of the new *Catharanthus* can be compared to plants of the male parent selection. Plants of the new *Catharanthus* differ primarily from plants of the male parent selection in the following characteristics:

1. Plants of the new *Catharanthus* have smaller flowers than plants of the male parent selection.
2. Plants of the new *Catharanthus* and the male parent selection differ in flower color as plants of the male parent selection have pale pink-colored flowers.

Plants of the new *Catharanthus* can be compared to plants of the *Catharanthus roseus* 'Sunnichitaro', disclosed in U.S. Plant Pat. No. 25,112. In side-by-side comparisons, plants of the new *Catharanthus* differed from plants of 'Sunnichitaro' in the following characteristics:

1. Plants of the new *Catharanthus* were broader than plants of 'Sunnichitaro'.
2. Plants of the new *Catharanthus* had thicker stems with shorter internodes than plants of 'Sunnichitaro'.

3. Plants of the new *Catharanthus* had smaller leaves than plants of 'Sunnichitaro'.
4. Plants of the new *Catharanthus* had smaller flowers than plants of 'Sunnichitaro'.
5. Flowers of plants of the new *Catharanthus* were darker red purple in color than flowers of plants of 'Sunnichitaro'. In addition, flowers of plants of 'Sunnichitaro' had a distinct eye zone.
6. Plants of the new *Catharanthus* had shorter peduncles than plants of 'Sunnichitaro'.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Suncatha 224' grown in a container.

The photograph at the bottom of the sheet comprises a close-up view of a typical flowering plant of 'Suncatha 224'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial production. During the production of the plants, day temperatures averaged 25° C. and night temperatures averaged 15° C. Plants were four months old when the description and photographs were taken. In the following description, color references are made to The Royal Horticultural Society Colour Chart, 2007 Edition, except where general terms of ordinary dictionary significance are used.

Botanical classification: *Catharanthus roseus* 'Suncatha 224'.

Parentage:

*Female, or seed, parent*.—Proprietary selection of *Catharanthus roseus* identified as code designation FS-S, not patented.

*Male, or pollen, parent*.—Proprietary selection of *Catharanthus roseus* identified as code designation NCPS, not patented.

Propagation:

*Type*.—By vegetative cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; white in color.

*Rooting habit*.—Freely branching; medium density.

Plant description:

*Plant and growth habit*.—Upright to outwardly spreading and mounding plant habit; freely branching habit, about four basal branches each with about seven secondary branches developing per plant; vigorous growth habit.

*Plant height*.—About 24.3 cm.

*Plant diameter*.—About 52 cm.

Lateral branch description:

*Length*.—About 23.2 cm.

*Diameter*.—About 4.3 mm.

*Internode length*.—About 1 cm.

*Strength*.—Strong.

*Aspect*.—Upright to outwardly.

*Texture*.—Pubescent.

*Color*.—Close to 145B.

Leaf description:

*Arrangement*.—Opposite, simple.

*Length*.—About 3.7 cm.

*Width*.—About 1.4 cm.

*Shape*.—Elliptic.

*Apex*.—Acute.

*Base*.—Obtuse.

*Margin*.—Entire.

*Texture, upper surface*.—Smooth, glabrous.

*Texture, lower surface*.—Pubescent.

*Venation pattern*.—Pinnate; reticulate.

*Color*.—Developing leaves, upper surface: Close to 137C. Developing leaves, lower surface: Close to 137D. Fully expanded leaves, upper surface: Close to 137B; venation, close to 144C. Fully expanded leaves, lower surface: Close to 137D; venation, close to 144D.

*Petioles*.—Length: About 4.1 mm. Diameter: About 1.4 mm. Texture, upper and lower surfaces: Pubescent. Color, upper and lower surfaces: Close to 145C.

Flower description:

*Flower arrangement and habit*.—Single salverform flowers arising from upper leaf axils; freely flowering habit with numerous flowers developing per plant; flowers face mostly upright to outwardly.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.3 cm. Diameter: About 2.5 mm. Shape: Cylindrical. Color: Close to 63B to 63C.

*Flower diameter*.—About 2.3 cm.

*Flower length* (*depth*).—About 2.2 cm.

*Tube length*.—About 1.9 cm.

*Tube diameter, at the base*.—About 1.5 mm.

*Corolla*.—Arrangement: Five petals in a single whorl fused at the base into a tube. Petal length from throat: About 1.1 cm. Petal width: About 5.7 mm. Petal shape: Oblanceolate. Petal apex: Acute. Petal margin: Entire. Petal texture, upper and lower surfaces: Smooth, glabrous. Throat texture: Smooth, glabrous. Tube texture: Smooth, glabrous. Color: Petal, when opening, upper surface: Close to N57B; towards the throat, close to 60B. Petal, when opening, lower surface: Close to 60D and 62C. Petal, fully opened, upper surface: Close to N66B; color does not fade with development. Petal, fully opened, lower surface: Close to 63C and 62D; color does not fade with development. Throat: Close to 145B. Tube: Close to 145B tinged with close to 181C.

*Calyx*.—Arrangement: Star-shaped tubular calyx with five sepals fused towards the base. Sepal length: About 1.7 mm. Sepal width: About 1 mm. Sepal shape: Lanceolate to narrowly deltoid. Sepal apex: Acute. Sepal margin: Entire. Sepal texture, upper and lower surfaces: Smooth, glabrous. Color, immature and mature, upper surface: Close to 144A. Color, immature and mature, lower surface: Close to 144A.

*Peduncles*.—Length: About 1.6 mm. Diameter: About 0.8 mm. Angle: Upright to outwardly. Strength: Strong. Texture: Smooth, glabrous. Color: Close to 145A.

*Reproductive organs*.—Stamens: Quantity per flower: Five. Stamen length: About 1.4 mm. Anther shape: Narrowly elliptic. Anther size: About 1.3 mm by 0.4 mm. Anther color: Close to 150D. Pollen amount: Scarce. Pollen color: Close to NN155D. Pistils: Quantity per flower: One. Pistil length: About 1.6 cm. Style color: Close to 145D. Stigma shape: Narrowly ellipsoidal. Stigma color: Close to 145B. Ovary color: Close to 144A.

*Seeds and fruits*.—Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Suncatha 224' as illustrated and described.

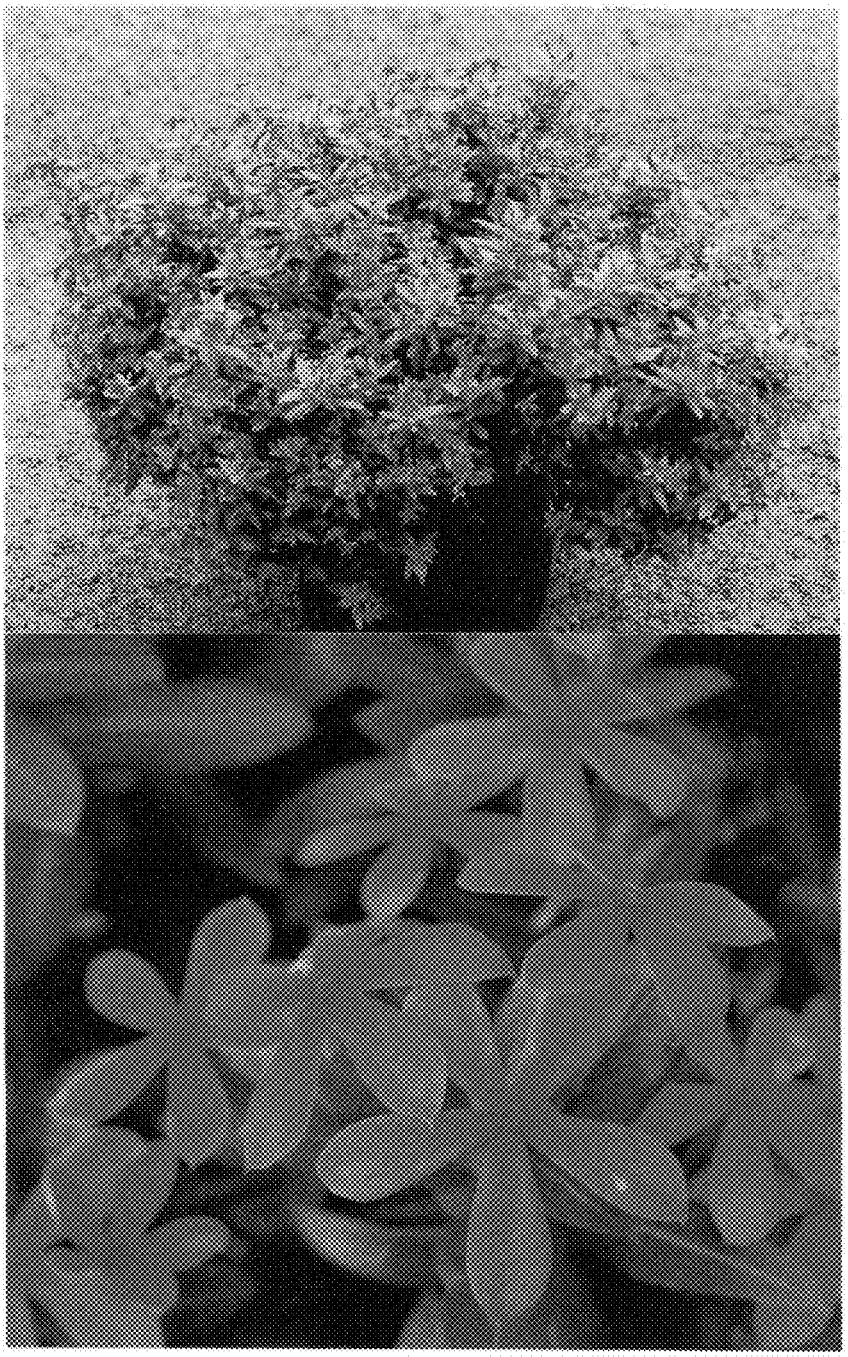

* * * * *